(12) United States Patent
Hewitt et al.

(10) Patent No.: US 8,652,146 B2
(45) Date of Patent: Feb. 18, 2014

(54) SHAPEABLE RETRIEVAL DEVICE AND METHOD OF USING

(75) Inventors: David R. Hewitt, Eden Prairie, MN (US); Ted J. Prukop, Ladera Ranch, CA (US); James D. Segermark, Gem Lake, MN (US)

(73) Assignee: Merit Medical Systems, Inc., South Jordan, UT (US)

( * ) Notice: Subject to any disclaimer, the term of this patent is extended or adjusted under 35 U.S.C. 154(b) by 83 days.

(21) Appl. No.: 13/014,427

(22) Filed: Jan. 26, 2011

(65) Prior Publication Data

US 2012/0029526 A1 Feb. 2, 2012

Related U.S. Application Data

(60) Provisional application No. 61/336,832, filed on Jan. 27, 2010.

(51) Int. Cl.
*A61B 17/24* (2006.01)
*A61B 17/26* (2006.01)

(52) U.S. Cl.
USPC ........................................................ 606/113

(58) Field of Classification Search
USPC .................. 606/108, 110–115, 127, 2.5, 128; 600/562, 564
See application file for complete search history.

(56) References Cited

U.S. PATENT DOCUMENTS

| 5,171,233 | A | 12/1992 | Amplatz et al. |
|---|---|---|---|
| 5,290,294 | A | 3/1994 | Cox et al. |
| 5,352,219 | A | 10/1994 | Reddy |
| 5,417,684 | A | 5/1995 | Jackson et al. |
| 5,460,610 | A | 10/1995 | Michael |
| 5,562,678 | A | 10/1996 | Booker |
| 5,613,973 | A | 3/1997 | Jackson et al. |
| 5,782,839 | A | 7/1998 | Hart et al. |
| 5,860,987 | A | 1/1999 | Ratcliff et al. |
| 5,911,725 | A | 6/1999 | Boury |
| 6,059,796 | A | 5/2000 | Bilitz et al. |
| 6,071,233 | A | 6/2000 | Ishikawa et al. |
| 6,174,318 | B1 | 1/2001 | Bates et al. |
| 6,458,145 | B1 | 10/2002 | Ravenscroft et al. |
| 6,517,550 | B1 | 2/2003 | Konya et al. |
| 2002/0123698 | A1 * | 9/2002 | Garibotto et al. ............. 600/585 |
| 2002/0188262 | A1 | 12/2002 | Abe |
| 2003/0212446 | A1 * | 11/2003 | Kaplan et al. ................. 607/129 |
| 2004/0059345 | A1 | 3/2004 | Nakao et al. |
| 2004/0068226 | A1 | 4/2004 | Brannon |
| 2004/0153095 | A1 * | 8/2004 | Seddon ......................... 606/113 |

(Continued)

FOREIGN PATENT DOCUMENTS

WO WO02/043600 6/2002

OTHER PUBLICATIONS

U.S. Appl. No. 13/106,995, filed May 13, 2011, Segermark.
U.S. Appl. No. 13/105,653, filed May 11, 2011, Segermark et al.

(Continued)

*Primary Examiner* — Thomas McEvoy
(74) *Attorney, Agent, or Firm* — Stoel Rives LLP (57) ABSTRACT

A retrieval device with a shapeable snare shaft for use in minimally invasive medical procedures. The retrieval device may further comprise a delivery conduit configured to receive both a snare shaft and a guidewire in one or more lumens. The retrieval device may also include a snare loop at both ends of the snare shaft.

14 Claims, 9 Drawing Sheets

(56) References Cited

U.S. PATENT DOCUMENTS

| | | | |
|---|---|---|---|
| 2005/0234474 A1* | 10/2005 | DeMello et al. | 606/113 |
| 2006/0090761 A1 | 5/2006 | Kurrus | |
| 2006/0116702 A1 | 6/2006 | Goto et al. | |
| 2007/0129719 A1* | 6/2007 | Kendale et al. | 606/41 |
| 2007/0162047 A1 | 7/2007 | Gasche | |
| 2007/0162048 A1 | 7/2007 | Quinn et al. | |
| 2007/0191866 A1 | 8/2007 | Palmer et al. | |
| 2007/0260264 A1* | 11/2007 | Nobis et al. | 606/113 |
| 2008/0086149 A1 | 4/2008 | Diamant et al. | |
| 2008/0188866 A1 | 8/2008 | Karpiel et al. | |
| 2009/0030427 A1 | 1/2009 | Razvi et al. | |
| 2009/0069806 A1* | 3/2009 | De La Mora Levy et al. | 606/46 |
| 2009/0112244 A1 | 4/2009 | Freudenthal | |
| 2009/0131749 A1 | 5/2009 | Ahmed et al. | |
| 2010/0087781 A1 | 4/2010 | Adams et al. | |

OTHER PUBLICATIONS

International Search Report and Written Opinion dated Mar. 18, 2011 for PCT/US2011/022509.
International Search Report and Written Opinion dated May 1, 2012 for PCT/US2012/020204.
International Search Report and Written Opinion dated May 3, 2012 for PCT/US2012/020208.
International Search Report and Written Opinion dated Aug. 13, 2012 for PCT/US12/36144.
International Search Report and Written Opinion dated Aug. 16, 2012 for PCT/US12/36125.
Office Action dated Sep. 26, 2012 for U.S. Appl. No. 13/106,995.
Office Action dated Mar. 13, 2013 for U.S. Appl. No. 13/105,653.
Office Action dated Mar. 28, 2013 for U.S. Appl. No. 13/343,570.
U.S. Appl. No. 13/343,570, filed Jan. 4, 2012, Lampropoulos et al.
U.S. Appl. No. 13/343,550, filed Jan. 4, 2012, Lampropoulos et al.
Office Action dated Jul. 19, 2013 for U.S. Appl. No. 13/343,570.

* cited by examiner

SHAPEABLE RETRIEVAL DEVICE AND METHOD OF USING

RELATED APPLICATIONS

This application claims priority to U.S. Provisional Application No. 61/336,832 filed on Jan. 27, 2010, the entire contents of which are hereby incorporated herein by reference.

TECHNICAL FIELD

The present disclosure relates generally to devices used to retrieve or manipulate items or structures located in anatomically remote locations, such as items located in body lumens. More specifically, the present disclosure relates to snare devices and methods for their use.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

A snare device may be configured to allow a practitioner to change the shape of the snare device during a therapeutic procedure. Such a device may allow a practitioner to more precisely position the device with respect to the object to be retrieved and the surrounding body lumen. Precise positioning of a snare device may enable a practitioner to more quickly and efficiently perform the needed therapy. Further, precise positioning may lessen trauma at the therapy site, minimizing injury from unwanted contact between the snare and portions of the body lumen. For example, precise positioning of the snare loop may reduce the possibility that the snare loop will rotate (or "whip") during therapy, which rotation can damage the inner lining of blood vessels.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use.

"Delivery conduit," as used herein, refers to an artificial channel capable of establishing communication between a remote location and an external environment. For example, in certain embodiments described herein, the delivery conduit comprises the outer sheath of a snare device, which in some embodiments comprises a catheter.

A used herein "fragment" means either a foreign object disposed within a body lumen or an anatomical structure within the body which requires ligation or removal.

Further, as used herein, a "snare device" refers to a medical device with an elongate shape having at least one "snare loop." Thus, a snare device may or may not include a delivery conduit or outer sheath member. As used herein a "snare loop" refers to a closed shape configuration of an elongate member such as a wire. The term is not limited to "loops" with generally circular shapes, but includes any variety of shapes, including, for example, square loops, rectangular loops, ellipsoidal loops, trapezoidal loops, etc.

Finally, as used herein, the term "shapeable" refers to a component that retains approximately at least 25% of its shape when it is (1) plastically deformed or shaped, (2) coupled with a second component which tends to deform the first component from its shaped state (such as to its original shape), and (3) removed from the second component. For example, a shaft which is initially substantially straight, deformed with an angular bend, then placed in a sheath which tends to hold the shaft in a straight position is "shapeable" if the shaft retains approximately at least 25% of the angle of the deformation when it is removed from the sheath. Similarly, the term "shaped" refers to components that are pre-shaped, which tend to retain their shape and cannot be readily plastically deformed. For example, a snare loop formed from a memory alloy with a given shape which is placed in a sheath which constrains that shape may be said to be "shaped" if the snare loop returns to its original shape when removed from the sheath.

Figure 1:
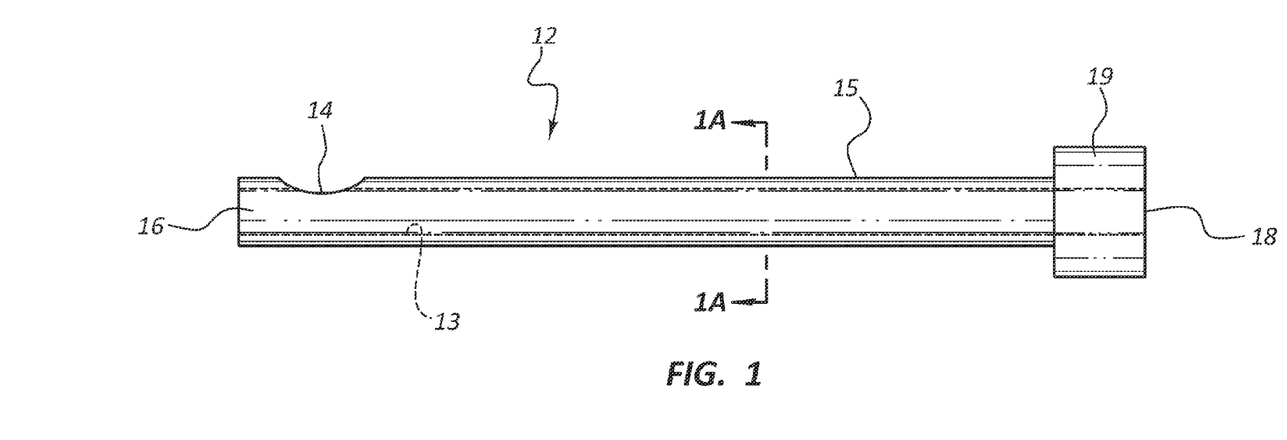
FIG. 1 is a side view of a delivery conduit having a single lumen.
Figure 1A:
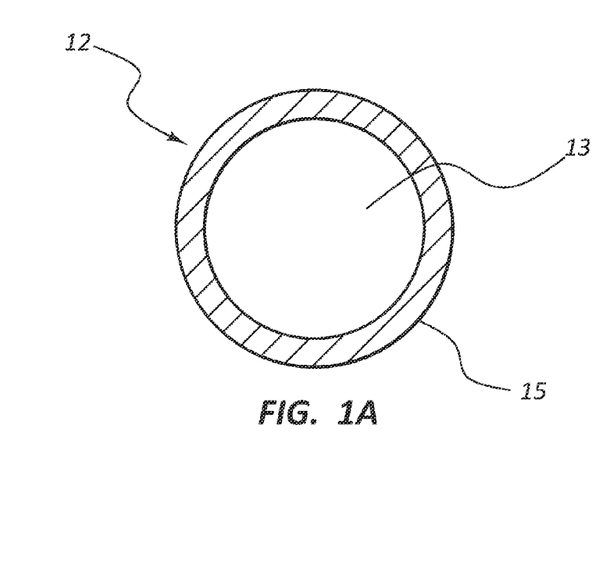
FIG. 1A is a cross sectional view taken through lines 1A-1A of the delivery conduit of FIG. 1.

Referring now to FIG. 1 which is a side view of a delivery conduit 12 having a single lumen 13. In the illustrated embodiment, the lumen 13 extends the length of the delivery conduit 12, from the proximal end 18 of the delivery conduit 12 to the distal end 16 of the delivery conduit 12. As also shown in FIG. 1A, the delivery conduit 12 and the lumen 13 may define a side wall 15 of the delivery conduit. The side wall 15 may be defined as the portion of the delivery conduit 12 surrounding the lumen where the outer surface of the side wall runs generally parallel to the longitudinal axis of the delivery conduit 12. In some embodiments, the delivery conduit may have a side port 14, or an opening in the side wall 15 of the delivery conduit 12.

In certain embodiments the delivery conduit 12 may also be configured with a connector 19 to couple the delivery conduit 12 to another device. This connector 19 may be any type of connector known in the art, for example a Luer connector.

In the illustrated embodiment the side port 14 extends through the side wall 15 of the delivery conduit 12 allowing access from the lumen 13 to an area outside the delivery conduit 12. In one embodiment the side port 14 constitutes a removed area of from about 5% to about 48% of the circumference of the side wall 15 of the delivery conduit. In other embodiments the side port 14 may fall into a smaller range of values, for example from about 25% to about 48% of the circumference of the delivery conduit.

In some embodiments the distal end 16 of the delivery conduit 12 may be open, creating an end port, or distal opening in the distal tip of the delivery conduit 12. In such embodiments, the lumen 13 extends through the end of the delivery conduit 12 at the distal end 16. It other embodiments the lumen 13 may not extend through the distal end 16 of the delivery conduit 12. It will be appreciated that in some embodiments the delivery conduit 12 will have such an opening at the distal end 16 in addition to a side port 14, whereas in other embodiments the delivery conduit 12 will only have a side port 14 with no opening at the distal end 16. In still further embodiments the delivery conduit will only have an opening at the distal end 16 and have no side port 14.

In embodiments where the delivery conduit 12 has an opening at the distal end 16, the opening may be configured to allow a guidewire (not shown) or other elongate medical device to extend through the distal end of the delivery conduit 12. In one embodiment the delivery conduit 12 may be configured such that the lumen 13 is sized to accommodate both a guidewire and the shaft of a snare device. In one example of such an embodiment, the guidewire may be configured to extend through an opening in the distal end 16 of the delivery conduit 12 and the snare device configured to extend through a side port 14. In other embodiments, both a guidewire and a snare device may extend through the same opening.

In certain embodiments the delivery conduit 12 defines an outer sheath through which medical devices (for example guidewires or snare devices) may pass during therapy. It will be appreciated that medical devices disposed within the delivery conduit 12 may be configured to be longitudinally displaceable with respect to the delivery conduit 12 during use.

The delivery conduit 12 may be made from any extrudable, medical grade plastic such as those commonly used for making catheters. Examples include but are not limited to polyurethane, polyethylene (varying densities), PET (polyethylene terephthalate), PVC, polypropylene, nylon, peba byx, ABS, Hytrel®, Santoprene®, polycarbonate, Kraton®, PES, PVDF, and FEP. The extruded plastic may be cut to length, followed by creation of the side opening 14 by conventional cutting or machining methods known in the art.

FIGS. 2-6 are side views of snare devices comprising shafts and snare loops. It will be appreciated that the illustrated embodiments have analogous features. The disclosure recited in connection with any embodiment may be applicable to any analogous feature in another embodiment, whether or not the components are numbered in both embodiments. Further, it will be appreciated that any of the snare devices illustrated or described in connection with any of FIGS. 2-6 may be used in any combination with any of the embodiments of delivery conduits disclosed in connection with FIGS. 1 and 1A. FIGS. 2A, 3A, 4A, 5A, and 6A are cross sectional views of the corresponding snare devices, but it will be appreciated that any of the disclosure or features recited in connection with any of these embodiments may analogously apply to every other embodiment or combination.

Figure 2:
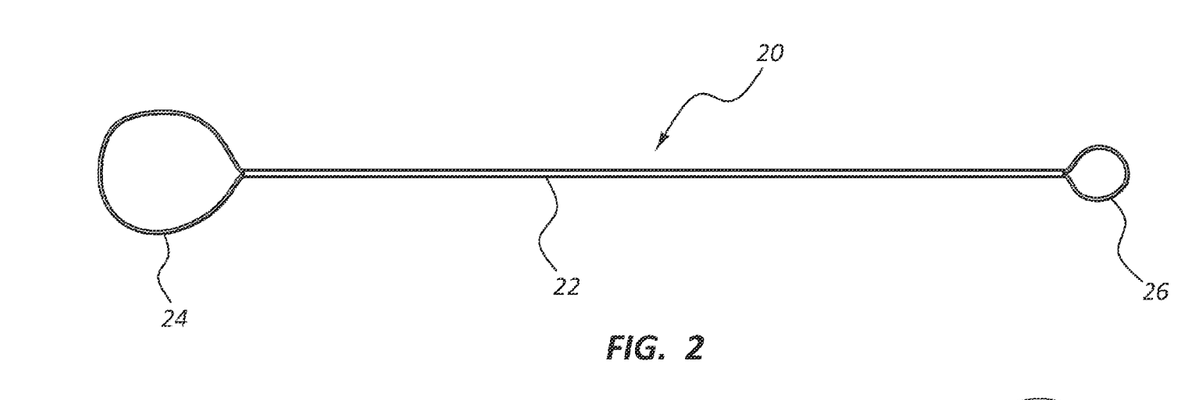
FIG. 2 is a side view of a snare device with two loops.

FIG. 2 is a side view of an embodiment of a snare device 20 comprising a first snare loop 24 attached to one end of a shaft 22 and a second snare loop 26 attached to an opposite end of the shaft 22. In this embodiment both the first snare loop 24 and the second snare loop 26 are configured to be in a generally circular configuration. In some embodiments the snare loops 24, 26 may be shaped. In other words, the circular configuration of the first snare loop 24 and the second snare loop 26 may be retained by constructing the first snare loop 24 and the second snare loop 26 of a superelastic material (such as a nickel titanium alloy, for example, nitinol). Superelastic materials may be able to be deformed to a much greater degree than ordinary materials without taking a permanent kink. It will be appreciated that in some embodiments only one of the two loops may be formed of a superelastic material, both loops may be so formed, or neither loop may be formed of a superelastic material.

In the embodiment illustrated in FIG. 2, the first snare loop 24 and the second snare loop 26 are configured to be of differing sizes. When utilizing such embodiments, a physician may discover during the procedure one size of snare loop 24, 26 may be preferred or required. Accordingly, in certain embodiments the physician can insert the snare device into a body lumen in such a manner as to utilize the desired snare loop 24, 26.

Figure 2A:
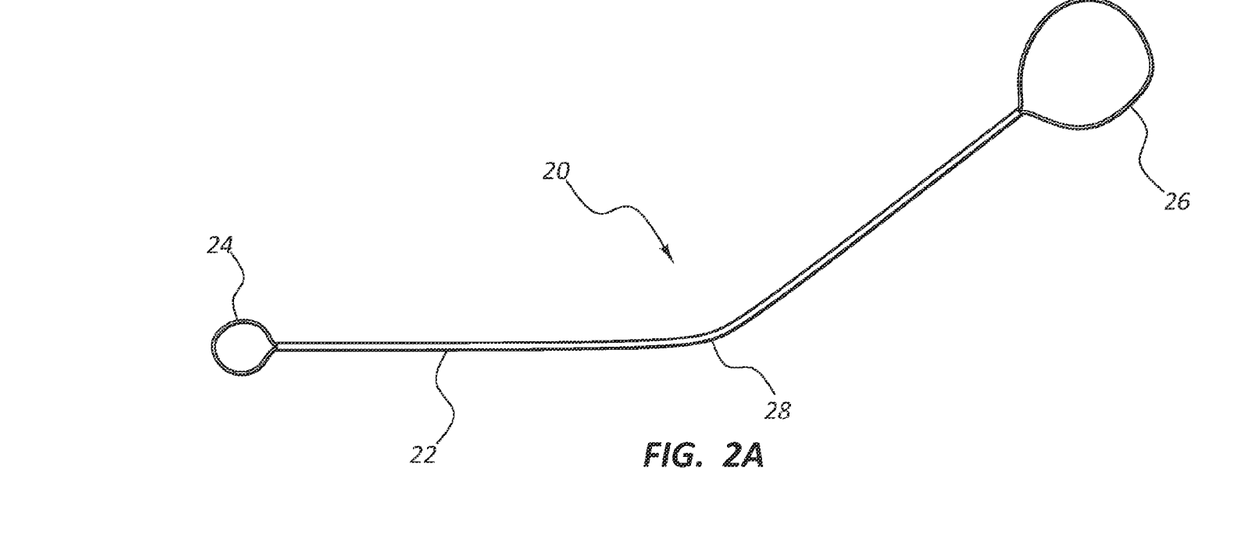
FIG. 2A is a side view of the snare device of FIG. 2, with a bend placed in the shaft of the device.

FIG. 2A is a side view of the snare device 20 shown in FIG. 2, wherein the shaft 22 has been configured to have a bend 28 along its length. In certain embodiments, the shaft 22 may be shapeable, that is, made of a material such as stainless steel which allows a permanent deformation to be placed in it prior to or during the procedure as determined by the physician.

Figure 3:
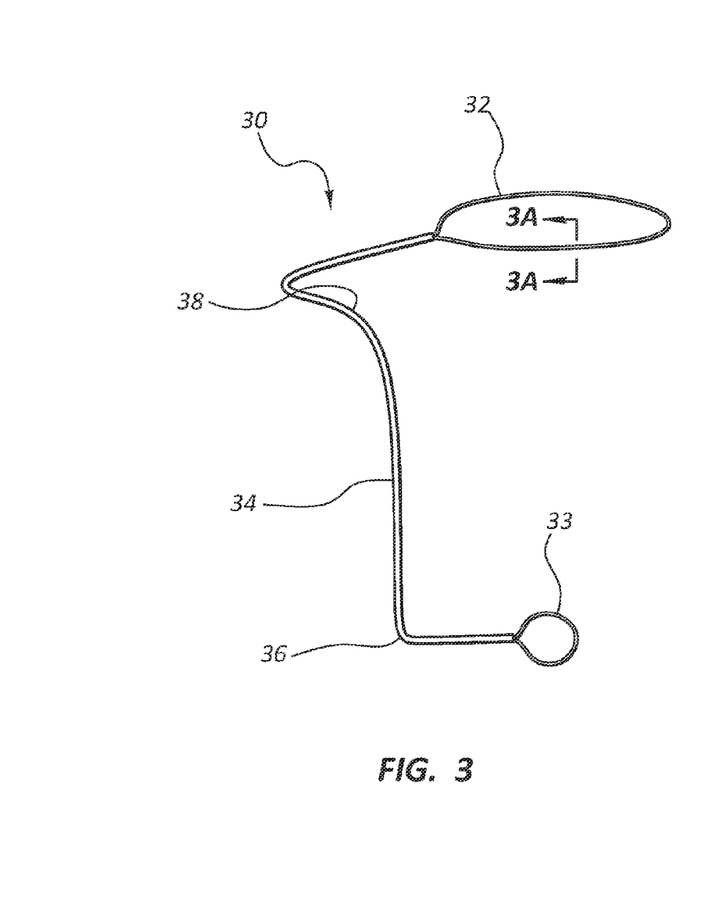
FIG. 3 is a side view of a snare device having with a loop at each end of the shaft portion and multiple bends in the shaft portion.
Figure 3A:
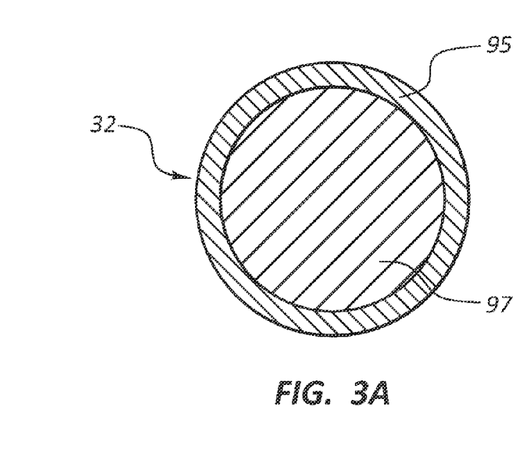
FIG. 3A is a cross sectional view taken through lines 3A-3A of the snare loop shown in FIG. 3.

FIG. 3 is a side view of another embodiment of a snare device 30 which has a shaft 34 configured with an angular bend 36 and an additional composite bend 38. In some embodiments bends 36, 38 will be formed during therapy and shaped according to an individual physician's preference. The shaft 34 may be made of a material such as stainless steel which allows a permanent deformation to be placed in it prior to or during the procedure as determined by the physician. As illustrated in FIG. 3, a first snare loop 32 having an elliptical configuration may be attached to one end of the shaft 34 and a second snare loop 33 having a circular configuration may be attached to an opposite end of the shaft 34. The elliptical configuration of the first snare loop 32 and the second snare loop 33 may be retained by constructing the first snare loop 32 and the second snare loop 33 of a of a superelastic material (such as a nickel titanium alloy, for example, nitinol).

Figure 4:
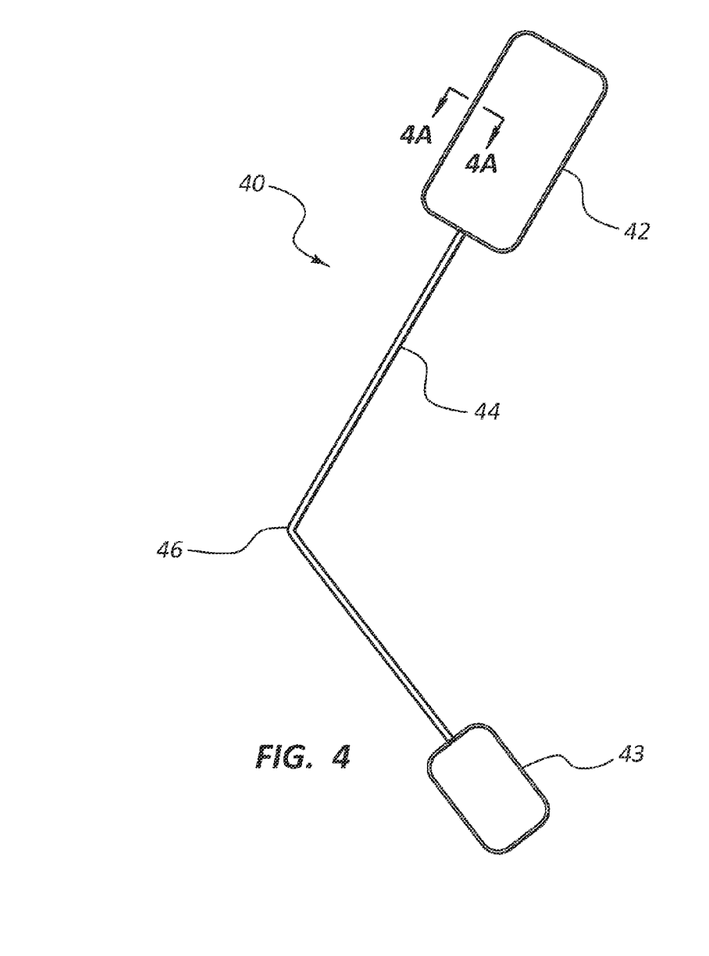
FIG. 4 is a side view of a snare device with two loops, each loop having a rectangular profile, and a shaft portion with a single angular bend.
Figure 4A:
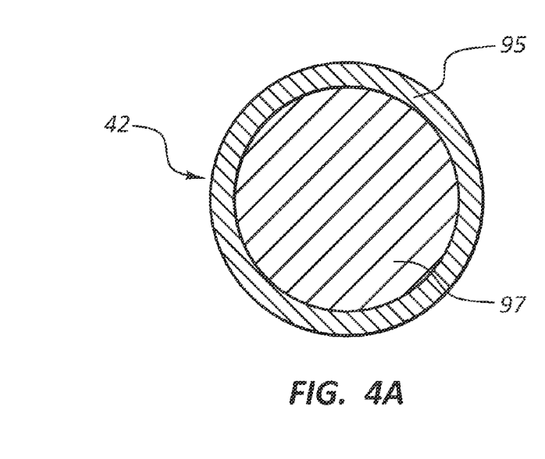
FIG. 4A is a cross sectional view taken through lines 4A-4A of the snare loop shown in FIG. 4.

FIG. 4 is a side view of an embodiment of a snare device 40 which has a shaft 44 configured with an angular bend 46. The shaft 44 may be made of a material such as stainless steel which allows a permanent deformation to be placed in it prior to or during the procedure as determined by the physician. In the illustrated embodiment, a first snare loop 42 having a rectangular configuration is attached to one end of the shaft 44 and a second snare loop 43 having a smaller rectangular configuration is attached to an opposite end of the shaft 44. The rectangular configuration of the first snare loop 42 and the second snare loop 43 may be retained by constructing the first snare loop 42 and the second snare loop 43 of a superelastic material.

Figure 5:
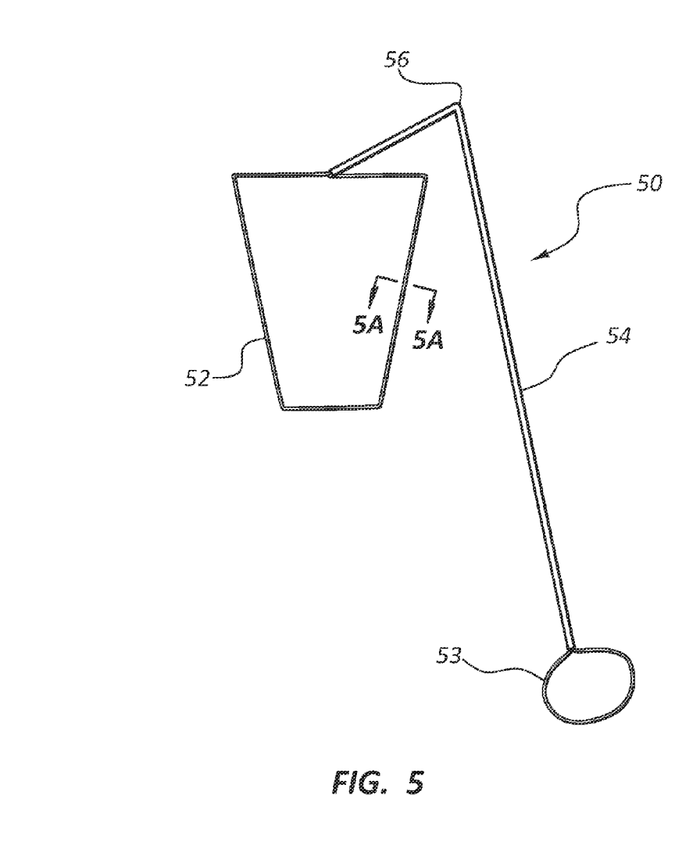
FIG. 5 is a side view of a snare device with a trapezoidal loop at one end of the shaft, a circular loop at another end of the shaft, and a single angular bend in the shaft.
Figure 5A:
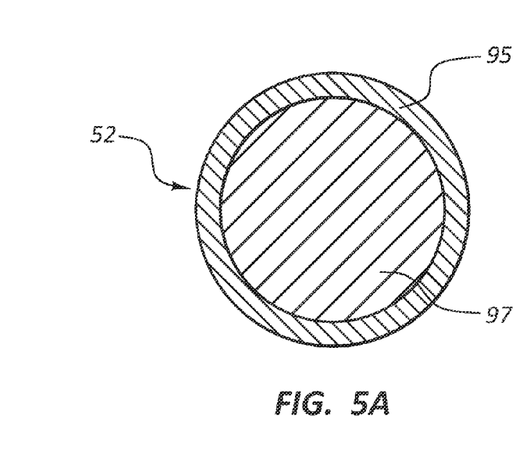
FIG. 5A is a cross sectional view taken through lines 5A-5A of the snare loop shown in FIG. 5.

FIG. 5 is a side view of yet another embodiment of a snare device 50 having a first snare loop 52 shaped into a trapezoidal configuration and a shaft 54 shaped to have a single, angular, bend 56. A second snare loop 53 in a circular configuration is attached to an opposite end of the shaft 54. The trapezoidal configuration of the first snare loop 52 and the circular configuration of the second snare loop 53 may be retained by constructing the first snare loop 52 and the second snare loop 53 of a superelastic material. The shaft 54 may be made of a material such as stainless steel which allows a permanent deformation to be placed in it prior to or during the procedure as determined by the physician.

Figure 6:
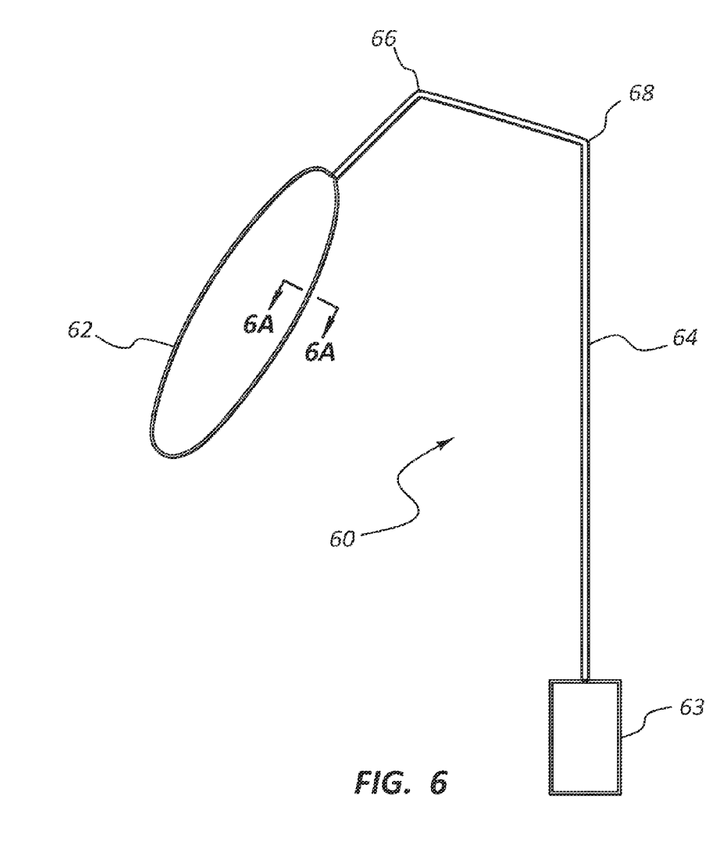
FIG. 6 is a side view of a snare device with an elliptical loop at one end of the shaft, a rectangular loop at another end of the shaft, and a shaft with multiple bends.
Figure 6A:
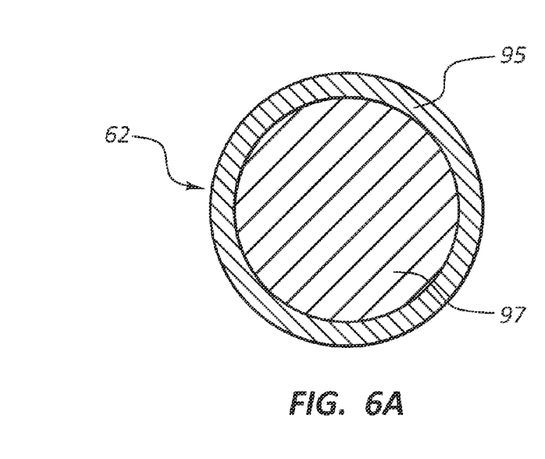
FIG. 6A is a cross sectional view taken through lines 6A-6A of the snare loop shown in FIG. 6.

FIG. 6 is a side view of an embodiment of a snare device 60 having a first snare loop 62 shaped into an elliptical configuration and a shaft 64 shaped to have a first angular bend 66, second angular bend 68 and a second snare loop 63 having a rectangular configuration. It is noted that, in this embodiment, the second snare loop 63 is smaller in dimension than the first snare loop 62. The elliptical configuration of the first snare loop 62 and the rectangular configuration of the second snare loop 63 may be retained by constructing the first snare loop 62 and the second snare loop 63 of a superelastic material. The shaft 64 may be made of a material such as stainless steel which allows a permanent deformation to be placed in it prior to or during the procedure as determined by the physician.

It will be understood that the specific configurations shown in FIGS. 2-6 are illustrative only and that many possible shapes and configurations are possible. For example, any size or shape of snare loop described above may be used in any combination with any other size or shape of snare loop disclosed or any shape or configuration of shaft disclosed. Further, the particular shapes, sizes, and configurations are illustrative only; it is within the scope of the current disclosure to modify these shapes and sizes in a manner known in the art.

In some embodiments, the shafts 22, 34, 44, 54, 64 as seen in FIGS. 2-6 are shipped in an unshaped configuration and may also be used without a physician shaping the shaft during the procedure.

As depicted in FIGS. 3A, 4A, 5A, and 6A, the snare loops 24, 26, 32, 33, 42, 43, 52, 53, 62, 63 may be radiopaque in nature. FIGS. 3A, 4A, 5A, 6A are cross sectional views taken through the snare loops 32, 42, 52, 62 and show a radiopaque coating 95 which surrounds the core wire 97. Though not shown in the figures, it will be understood that the snare loops 24, 26, 32, 33, 42, 43, 52, 53, 62, 63 may also be radiopaque in some embodiments. Radiopacity may be imparted to the snare loops by processes known to those having skill in the art, including but not limited to dipping, coating, plating, vapor deposition, coils, coverings, and sleeves. Exemplary radiopaque materials include platinum, and gold plated tungsten. In one embodiment only the snare loops 24, 26, 32, 33, 42, 43, 52, 53, 62, 63 are radiopaque, while in other embodiments (not shown) the radiopaque coating 95 may extend proximally further down the shafts 22, 34, 44, 54, 64.

The snare devices 20, 30, 40, 50, 60 may be made by obtaining a shapeable wire of a thickness (in some embodiments between about 0.014-0.018 inches) suitable to maintain a bend, for the shaft portions 22, 34, 44, 54, 64, followed by cutting the wire to length. Suitable shaft materials include but are not limited to 304 stainless steel and 316 stainless steel, and could also include any non-superelastic material able to be quickly and easily shaped. In one embodiment, the snare loop 24, 26, 32, 33, 42, 43, 52, 53, 62, 63 is attached to a more proximal point of the shaft wire and attached by conventional attachment methods known in the art, including but not limited to welding, adhesives, ball-and-socket techniques, cinching mechanisms, and mechanical fasteners. When completed, the joined area (not shown) may be substantially flush with the wire so as to minimize the occurrence of rough or inequitable areas that could cause tissue damage upon deployment.

Radiopacity may be imparted to the snare loops 24, 26, 32, 33, 42, 43, 52, 53, 62, 63 by applying a radiopaque coating 95 by conventional methods as discussed above. Following curing of the radiopaque coating 95 the snare wire 20, 30, 40, 50, 60 may be sterilized and loaded into a delivery conduit 12 with the proximal end being inserted through the proximal opening 18.

FIGS. 7A-8D illustrate embodiments of snare devices where shaft members such as those disclosed in connection with FIGS. 2-6 and 2A-6A are coupled to a delivery conduit such as that described in connection with FIGS. 1 and 1A.

FIGS. 7A-7D illustrate a snare device 10 comprising a single lumen 13 with a snare shaft 22 and a guidewire 90 disposed within the lumen 13. In the illustrated embodiment the delivery conduit 12 is configured with a side port 14 and an opening at the distal end of the delivery conduit. The guidewire is configured to extend through the opening in the distal end of the delivery conduit 12 and the snare loop and shaft configured to extend through the side port 14. FIGS. 7A-7D illustrate a single lumen delivery conduit 12 in multiple stages of deployment, including trapping a fragment F.

Figure 8A:
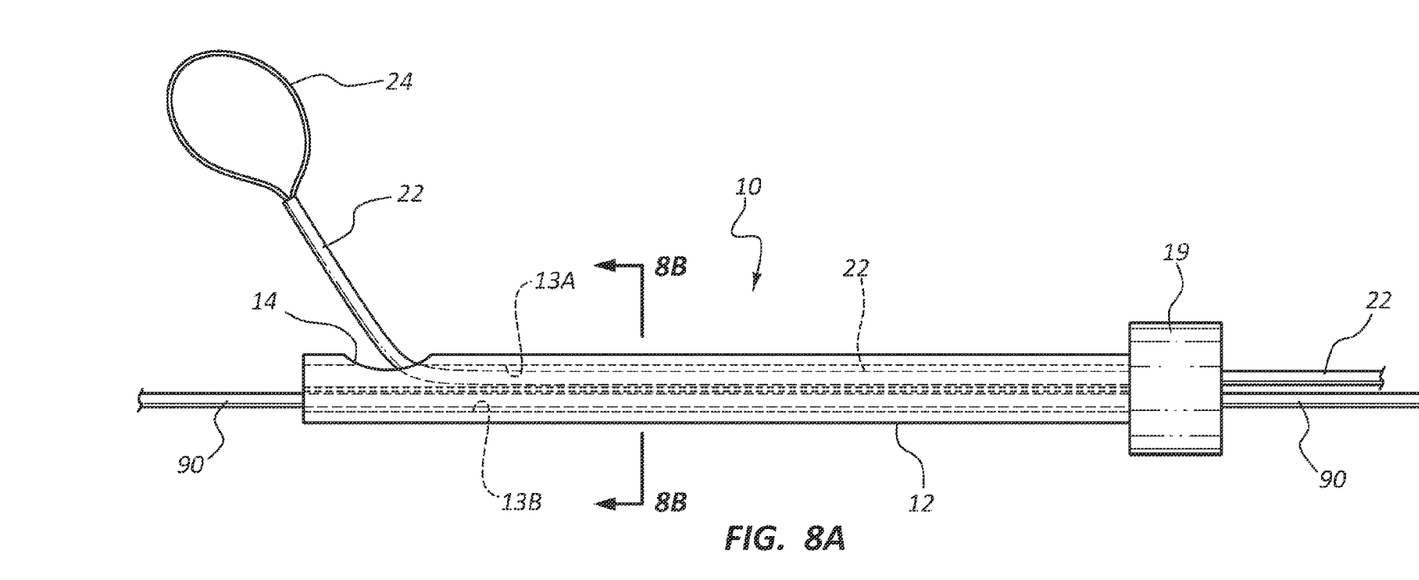
FIG. 8A is a side view of a snare device having a delivery conduit with two lumens.

FIGS. 8A-8D illustrate embodiments of a snare device 10 with two lumens 13A, 13B. FIG. 8A illustrates a snare device 10 comprising a delivery conduit 12 with two lumens 13A, 13B, a snare shaft 22 and loop 24, and a guidewire 90. In the illustrated embodiment, the snare shaft 22 is disposed within lumen 13A and the guidewire within lumen 13B. As illustrated, lumen 13A may have a side port 14 configured to allow communication between lumen 13A and an area outside the delivery conduit 12. In addition to side port 14, lumen 13A may also be configured with an opening at the distal end of the delivery conduit 12. Similarly, lumen 13A could include an opening at the distal end of the delivery conduit without a side port 14. In the illustrated embodiment, lumen 13B is configured with an opening at the distal end of the delivery conduit 12. Similar to lumen 13A, lumen 13B could also be configured only with a side port, only with an opening at the distal end of the delivery conduit, or both. Furthermore, though the illustrated embodiment shows guidewire 90 disposed within lumen 13B and snare shaft 22 disposed within lumen 13A, in other embodiments, lumen 13A may be configured to receive a guidewire and lumen 13B configured to receive a snare shaft.

Figure 8B:
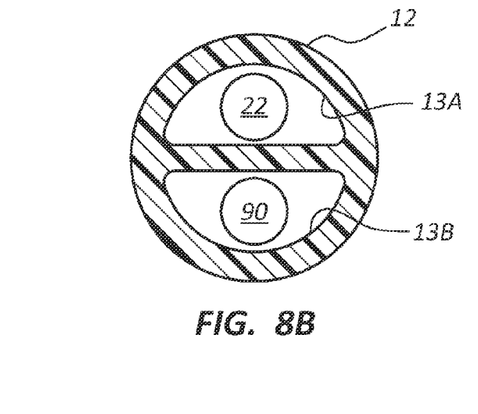
FIG. 8B is a cross sectional view of the delivery conduit taken through lines 8B-8B.
Figure 8C:
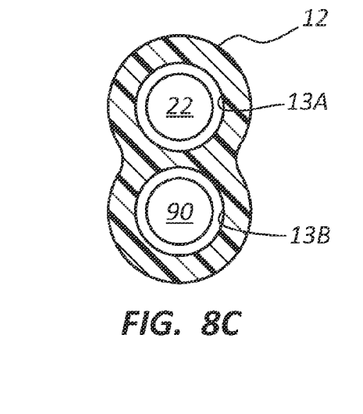
FIG. 8C is a cross sectional view of another embodiment of a delivery conduit with two lumens.
Figure 8D:
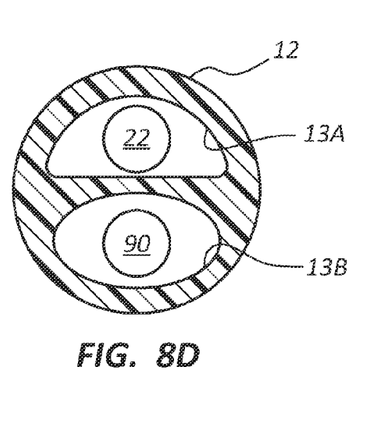
FIG. 8D is a cross sectional view of yet another embodiment of a delivery conduit with two lumens.

FIGS. 8B-8D illustrate cross sectional views of certain embodiments of a two lumen delivery conduit. The delivery conduit may have a substantially circular cross section with semicircular lumens at in FIG. 8B, a "FIG. 8" cross section with circular lumens as in FIG. 8C, a circular cross section with one semicircular lumen and one rounded (either circular or elliptical) lumen as in FIG. 8D, or any combination of delivery conduit and lumen cross sectional shapes. For example, a delivery conduit may also have a circular cross section with two circular or elliptical lumens disposed within it. In FIG. 8D a guidewire 90 is disposed within the elliptical lumen 13B and the snare shaft 22 within the semicircular lumen 13A. It will be appreciated that in other embodiments the lumen configured to receive the guidewire 90 may be semicircular in shape while the lumen configured to receive the snare shaft 22 may be ellipsoidal.

In certain embodiments the delivery conduit may further include three or more lumens. For example, in one embodiment the snare device may have a first lumen configured to receive a snare shaft, a second lumen configured to receive a guidewire, and a third lumen configured to receive a balloon device.

FIGS. 7A-7D generally may be understood as illustrating potential relative positions of the components of the snare device 10 during therapy. The therapeutic procedure may involve any therapy in which snares or snare devices may be utilized such as removing a fragment (either a foreign object or body matter) from a lumen of the central venous system, for example. To use the device, the physician may first remove the snare device from a sterile package (not shown). A snare shaft 22 may be disposed within the delivery conduit 12 in the packaged configuration. A physician may remove the snare shaft 22 from the delivery conduit 12 by displacing the snare shaft 22 with respect to the delivery conduit 12 in a proximal direction. In embodiments where the snare shaft has a snare loop coupled to each end, the physician will determine which snare loop is desirable to perform the therapy.

Once the snare shaft 22 is removed from the delivery conduit, the physician may deform the snare shaft into a desired configuration. The desired configuration may include multiple bends (including compound bends), a single bend, or no bend at all. The physician may deform the shaft by use of human hands, by placement of the unshaped shaft over a mandrel, or any other means known in the art.

During therapy the delivery conduit 12 may be introduced into a body lumen of a patient. In some embodiments a guidewire 90 may be utilized to position the delivery conduit 12 and navigate the delivery conduit 12 through the body lumen. It will also be appreciated that the snare shaft 22 may be disposed within the delivery conduit 12 when the delivery conduit is initially introduced into the body lumen, or the snare shaft may be inserted into a lumen of the delivery conduit 12 after the delivery conduit is disposed within a body lumen of the patent. Further, the physician may: (A) remove the snare shaft 22 from the delivery conduit before the delivery conduit 12 is introduced into the body, shape the snare shaft 22, and reinsert the snare shaft 22 into the delivery conduit 12 before the delivery conduit is first introduced into the body; (B) the physician may first introduce the delivery conduit 12 (with the snare shaft 22 disposed inside) into the body, then remove the snare shaft 22 for shaping and reinsertion; (C) the physician may insert the delivery conduit 12 into the body lumen without the snare shaft 22 disposed inside, shape the snare shaft 22, then insert the snare shaft 22 into the delivery conduit 12; (D) or any other combination of these sequences. Furthermore, the physician may remove the snare shaft 22 from the delivery conduit 12 at any point during therapy for shaping or reshaping, regardless of whether the snare shaft 22 has already been shaped.

Figures 7A, 7B:
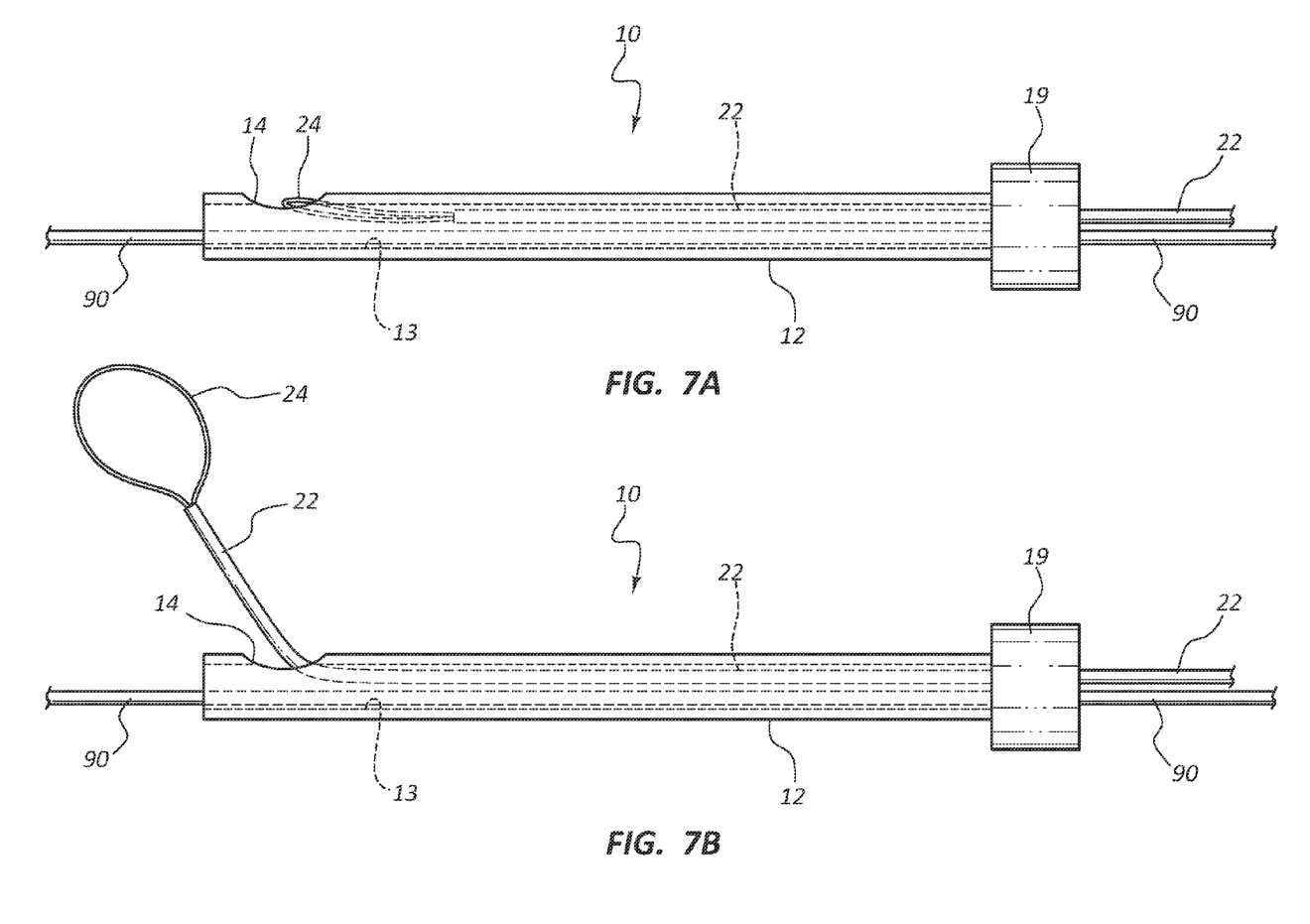
FIG. 7A is a side view of an embodiment of a snare device with a delivery conduit and a guidewire.
FIG. 7B is a side view of the snare device of FIG. 7A with the snare loop extended from the delivery conduit.
Figure 7C:
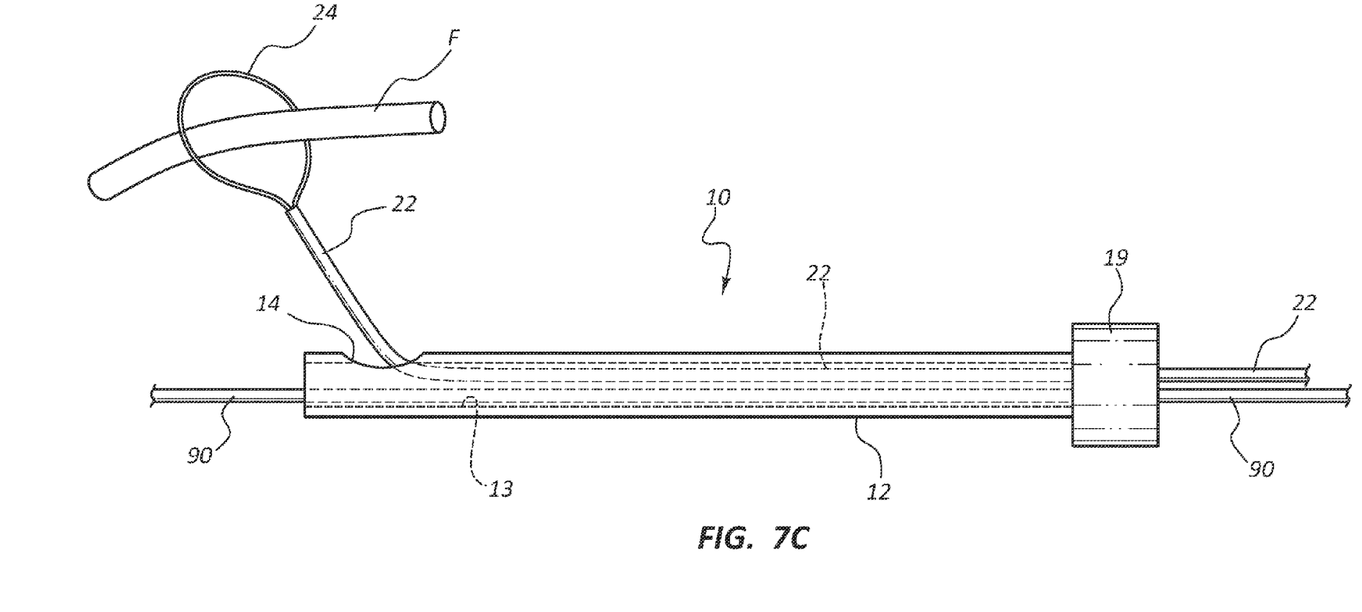
FIG. 7C is a side view of the snare device of FIGS. 7A and 7B with the snare loop extended from the delivery conduit and surrounding a fragment.
Figure 7D:
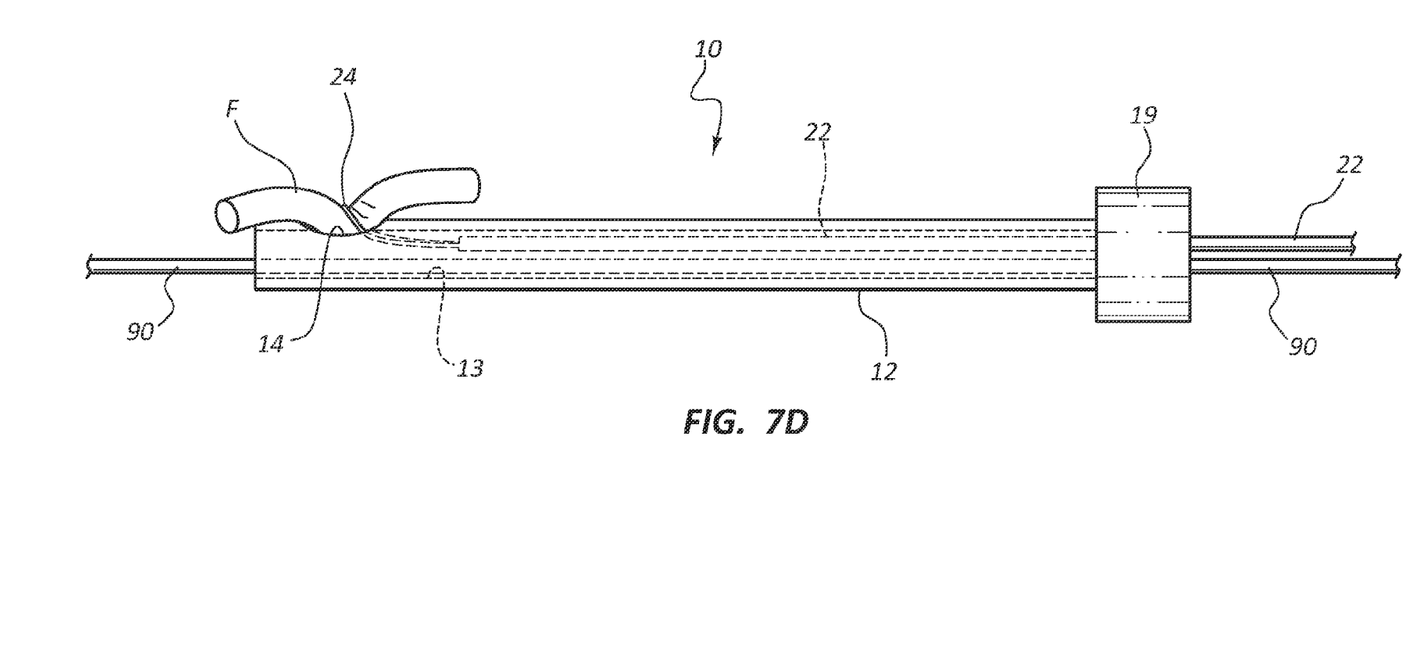
FIG. 7D is side view of the snare device of FIGS. 7A, 7B, and 7C with the snare loop drawn partially into the lumen such that the fragment is trapped between the loop and the delivery conduit.

Once the delivery conduit 12 and snare shaft 22 are positioned and shaped for therapy, the physician may deploy the snare loop 24 by displacing the snare shaft 22 in a distal direction relative to the delivery conduit 12. As illustrated in FIG. 7A-7D, the snare loop 24 may then be manipulated to surround the fragment F. Once the snare loop 24 is in place, the physician may then displace the snare shaft 22 in a proximal direction with respect to the delivery conduit 12 such that the fragment F is trapped between the snare loop 24 and the delivery conduit 12, as shown in FIG. 7D. The snare device 10 may then be removed from the body lumen, thus removing the fragment F from the body.

In some embodiments it will be desirable to extend the guidewire 90 beyond the delivery conduit 12 (either through a distal opening or through a side port) prior to deploying the snare loop 24 beyond the delivery conduit 12. This sequence may reduce the frequency of instances wherein the snare loop 22 inadvertently captures or becomes entangled with the guidewire 90.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A snare device, comprising:
   an elongate outer sheath having proximal and distal ends and having a first lumen disposed within the outer sheath between the proximal and distal ends of the outer sheath, the first lumen having a proximal opening near the proximal end of the outer sheath and a distal opening near the distal end of the outer sheath;
   an elongate shapeable shaft having a first end and a second end, the elongate shapeable shaft configured to be disposed within the first lumen of the outer sheath;
   a first expandable snare loop non-adjustably coupled to the first end of the shaft, the first snare loop configured to be delivered through the outer sheath during use; and
   a second expandable snare loop non-adjustably coupled to the second end of the shaft, the second snare loop configured to be delivered through the outer sheath during use,
   wherein the first snare loop has a maximum circumscribable area which is larger than a maximum circumscribable area of the second snare loop;
   wherein the elongate shapeable shaft is configured to retain at least 25% of its shape when it is:
   plastically deformed by a user to a shaped state, the plastic deformation occurring while the elongate shapeable shaft is outside the sheath,
   disposed within the first lumen of the outer sheath such that the outer sheath tends to deform the elongate shapeable shaft from the shaped state, and
   the elongate shapeable shaft is removed from the sheath.

2. The snare device of claim 1, wherein the distal opening of the first lumen is located in a side wall of the outer sheath.

3. The snare device of claim 1, wherein the outer sheath further comprises a second lumen having a proximal opening near the proximal end of the sheath and a distal opening near the distal end of the sheath, the second lumen configured to receive a guidewire.

4. The snare device of claim 3, wherein the distal opening of the second lumen is located at the distal end of the outer sheath, such that the distal opening of the second lumen is located distal of the distal opening of the first lumen.

5. The snare device of claim 1, wherein at least one of the first snare loop or the second snare loop is coated with a radiopaque material.

6. A snare device, comprising:
an elongate outer sheath having proximal and distal ends and having a first lumen disposed within the outer sheath between the proximal and distal ends of the outer sheath, the first lumen having a proximal opening near the proximal end of the outer sheath and a distal opening near the distal end of the outer sheath;
an elongate shapeable shaft having a first end and a second end, the shaft configured to be disposed within the first lumen of the outer sheath;
a first expandable snare loop coupled to the first end of the shaft; and
a second expandable snare loop coupled to the second end of the shaft;
wherein the first snare loop has a maximum circumscribable area which is larger than a maximum circumscribable area of the second snare loop;
wherein the elongate shapeable shaft is configured to retain at least 25% of its shape when it is:
plastically deformed by a user to a shaped state, the plastic deformation occurring while the elongate shapeable shaft is outside the sheath,
disposed within the first lumen of the outer sheath such that the outer sheath tends to deform the elongate shapeable shaft from the shaped state, and
the elongate shapeable shaft is removed from the sheath.

7. The snare device of claim 6, wherein the distal opening of the first lumen is located in a side wall of the outer sheath.

8. The snare device of claim 6, wherein the outer sheath further comprises a second lumen having a proximal opening near the proximal end of the sheath and a distal opening near the distal end of the sheath, the second lumen configured to receive a guidewire.

9. The snare device of claim 8, wherein the distal opening of the second lumen is located at the distal end of the outer sheath, such that the distal opening of the second lumen is located distal of the distal opening of the first lumen.

10. The snare device of claim 6, wherein the first snare loop is coated with a radiopaque material.

11. A snare assembly, comprising:
an elongate outer sheath having proximal and distal ends and having a first lumen disposed within the outer sheath between the proximal and distal ends of the outer sheath, the first lumen having a proximal opening near the proximal end of the outer sheath and a first distal opening near the distal end of the outer sheath;
an elongate shapeable shaft having a first end and a second end, the shaft configured to be disposed within the first lumen of the outer sheath;
a first expandable snare loop coupled to the first end of the shaft;
a second expandable snare loop coupled to the second end of the shaft; and
a guidewire configured to be disposed within a lumen of the outer sheath;
wherein the first snare loop has a maximum circumscribable area which is larger than a maximum circumscribable area of the second snare loop;
wherein the elongate shapeable shaft is configured to retain at least 25% of its shape when it is:
plastically deformed by a user to a shaped state, the plastic deformation occurring while the elongate shapeable shaft is outside the sheath,
disposed within the first lumen of the outer sheath such that the outer sheath tends to deform the elongate shapeable shaft from the shaped state, and
the elongate shapeable shaft is removed from the sheath.

12. The snare assembly of claim 11, wherein: the first distal opening is in a side wall of the first lumen; the first lumen has a second distal opening located distal of the first distal opening; and wherein the first snare loop is configured to extend from the first distal opening and the guidewire is configured to extend from the second distal opening.

13. The snare assembly of claim 11, wherein the outer sheath further comprises a second lumen having a proximal opening near the proximal end of the outer sheath and a distal opening near the distal end of the outer sheath and wherein the guidewire is disposed within the second lumen, such that the distal opening of the second lumen is located distal of the distal opening of the first lumen.

14. The snare assembly of claim 13, wherein the first distal opening of the first lumen is located in a side wall of the outer sheath.

* * * * *